| United States Patent [19] | [11] Patent Number: 4,658,637 |
| Ollivaud et al. | [45] Date of Patent: Apr. 21, 1987 |

[54] CELL FOR ANALYZING A FLUID WHICH IS CONDENSABLE, AT LEAST IN PART

[75] Inventors: Bernard Ollivaud, Ligne; Jean-Marie Lebas, Basse Goulaine, both of France

[73] Assignee: Alsthom, Paris, France

[21] Appl. No.: 790,592

[22] Filed: Oct. 23, 1985

[30] Foreign Application Priority Data

Oct. 23, 1984 [FR] France .................. 84 16196

[51] Int. Cl.⁴ .......................................... G01N 25/00
[52] U.S. Cl. ..................................................... 73/61.3
[58] Field of Search .................... 73/53, 61.3, 64.2, 23

[56] References Cited

U.S. PATENT DOCUMENTS 2,380,082 7/1945 Sloan ........................................ 73/23
2,662,393 12/1953 Rzasa ..................................... 73/61.3 X

FOREIGN PATENT DOCUMENTS 2474196 12/1981 France .

Primary Examiner—Jerry W. Myracle
Assistant Examiner—J. W. Roskos
Attorney, Agent, or Firm—Sughrue, Mion, Zinn, Macpeak and Seas

[57] ABSTRACT

A cell (4) for analyzing a fluid which is condensable, at least in part. The cell comprises a volume (16, 17, 18) in which the fluid is inserted. The volume is delimited firstly by an envelope (11, 12, 13) and secondly by an upper piston (14) capable of sliding in a sealed manner in the envelope and associated with apparatus for adjusting the pressure of the fluid being analyzed, together with lower apparatus enabling the level of the gas/liquid separation surface to be adjusted. The envelope is provided with portholes (19) associated with marking in order to display and measure the level of the surface. Conduits (20, 21) are provided between the piston and said lower apparatus for inserting the fluid to be analyzed into the volume and for emptying the volume of the fluid. The cell includes the improvement whereby a rod (27) from a first hydraulic control actuator is linked to the upper piston and a lower piston (15) is connected to a rod (29) from a second hydraulic control actuator.

5 Claims, 2 Drawing Figures

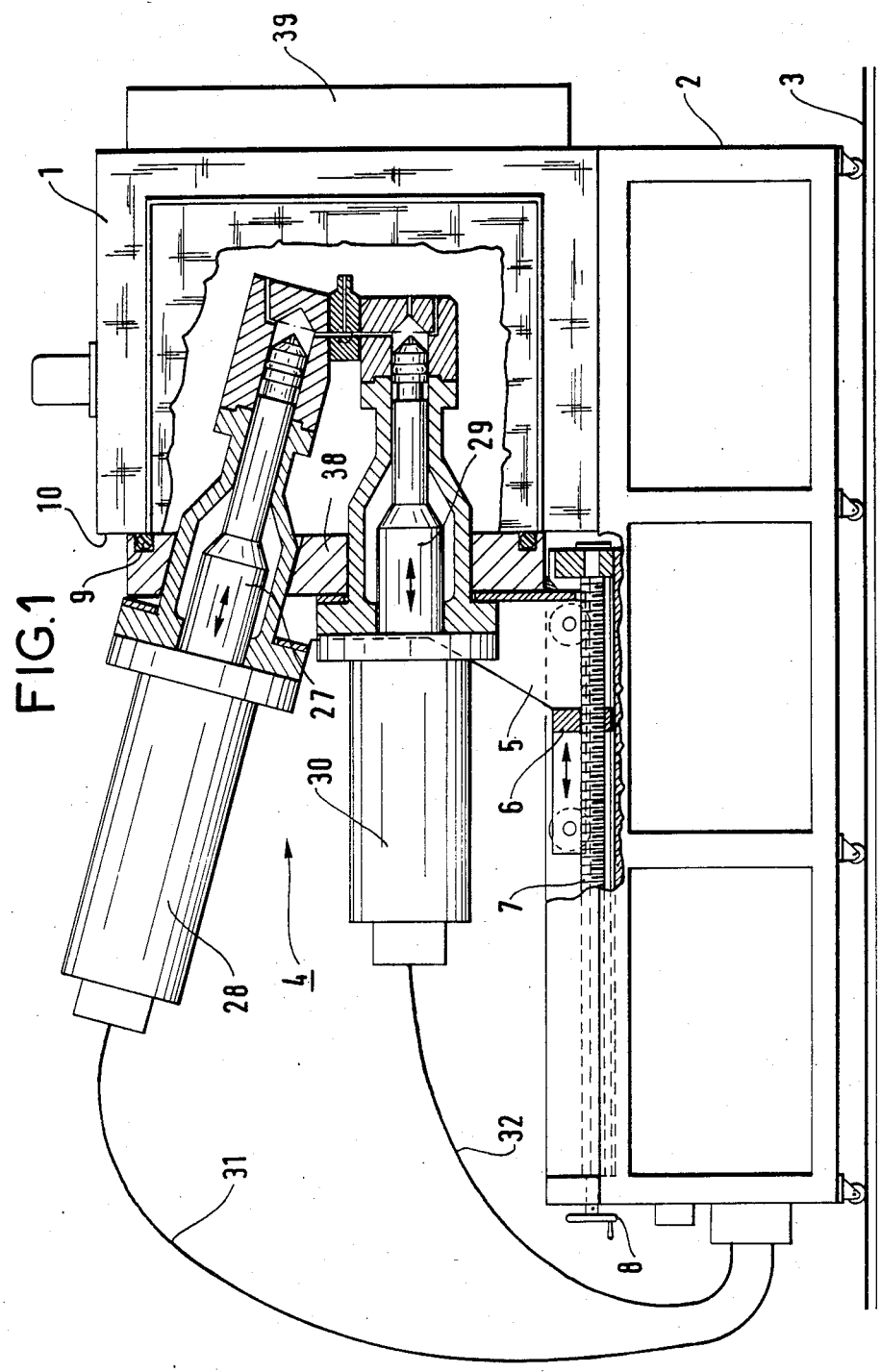

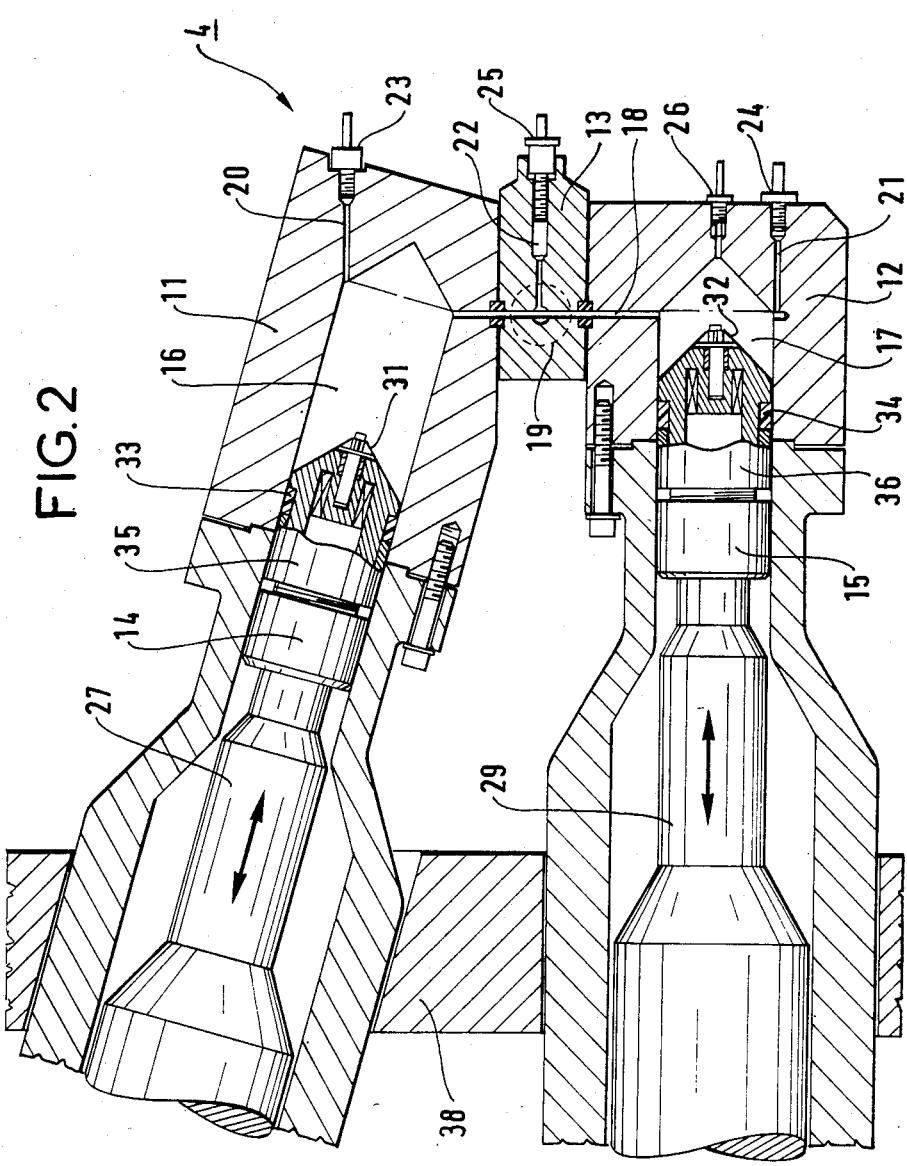

CELL FOR ANALYZING A FLUID WHICH IS CONDENSABLE, AT LEAST IN PART

The present invention relates to a cell for analyzing a fluid which is condensable, at least in part.

BACKGROUND OF THE INVENTION

Such cells are used, in particular, for analyzing the physical characteristics of pressure, volume and temperature of fluids from oil exploration wells, since a knowledge of these characteristics is fundamental in developing an oil field. Such cells are also used for analyzing light oils, for determining reservoirs, and also for various other applications such as investigating phase equilibrium, etc. They can be used for plotting various pressure curves as a function of temperature for given percentages of vapor phase relative to the total volume of fluid.

One such cell, described in U.S. Pat. No. 2,380,082 comprises a strong vertical cylindrical envelope having two superposed chambers therein, which chambers are in communication with each other, and the lower chamber has the smaller diameter. The envelope is provided with portholes looking into the lower chamber and with graduations for showing and measuring the level of the separation surface between the liquid phase and the gas phase of the fluid under investigation. The upper chamber includes a freely-mounted piston which divides said upper chamber into two portions. The upper portion is filled with mercury via a mercury pump and enables desired measuring pressures to be exerted on the free piston. The bottom end of the bottom chamber is also fed with mercury in order to bring the gas-liquid separation surface in the fluid under investigation to a suitable level. The liquid phase of said fluid is in direct contact with the mercury which acts as a piston. The cell is placed in a heated enclosure.

Such apparatus has the drawback of using mercury which is a dangerous material and which requires heavy equipment, in particular for pumping purposes. Further, the direct interface in the bottom chamber between the mercury and the liquid phase of the fluid under investigation requires special precautions to be taken or special equipment when the cell is being emptied of the fluid under investigation in order to ensure that only said fluid is removed without any mercury being mixed in. Finally, some fluids may contain components which react or form alloys or amalgams with mercury.

The present investigation thus seeks to provide such a cell which does not require the use of any mercury.

SUMMARY OF THE INVENTION

The present invention provides a cell for analyzing a fluid which is condensable, at least in part, said cell comprising a volume in which the fluid is inserted, said volume being delimited firstly by an envelope and secondly by an upper piston capable of sliding in a sealed manner in said envelope and associated with means for adjusting the pressure of the fluid being analyzed, together with lower means enabling the level of the gas/liquid separation surface to be adjusted, said envelope being provided with portholes associated with marking in order to display and measure the level of said surface, means being provided between the piston and said lower means for inserting the fluid to be analyzed into said volume and for emptying said volume of said fluid, the cell including the improvement whereby said means associated with the upper piston comprise a rod from a first control actuator linked to said upper piston, and whereby said lower means for adjusting the level of said gas/liquid separation surface include a lower piston connected to a rod from a second control actuator.

In a preferred embodiment of the invention, and in order to ensure that an error in measuring the level of the liquid/gas separation surface gives rise at worst to a very small error in volume, said internal volume of said envelope includes a restriction at the level of said portholes for observation and measurement, thus dividing said internal volume into an upper chamber and a lower chamber which are interconnected by said restriction which constitutes a connection channel.

In a preferred embodiment, said envelope includes three portions, namely an upper portion enclosing said upper chamber, an intermediate portion including said portholes and having said connection channel passing therethrough, and a lower portion enclosing said lower chamber, said lower portion and said second actuator being disposed horizontally, said upper portion and said first actuator being slightly inclined relative to the horizontal, and the intermediate portion being situated between said upper and lower portions at their ends which are closest together, said connection channel being vertical and opening out into the lowest point of said upper chamber.

Advantageously, said inclination is about 15°.

Each piston may be provided with an agitator device on its side furthest from its connection with its actuator rod.

BRIEF DESCRIPTION OF THE DRAWINGS

An embodiment of the invention is now described by way of example, with reference to the accompanying drawings, in which:

FIG. 1 shows an installation for analyzing fluids and including a cell in accordance with the invention;

FIG. 2 is a view on a larger scale showing the cell in accordance with the invention.

MORE DETAILED DESCRIPTION

With reference to FIG. 1, the equipment comprises a thermostatic chamber 1 whose temperature may be adjusted over the range $-20°$ C. $+200°$ C., said enclosure is mounted on a frame 2 which is movable on rails 3, and encloses the cell 4 per se.

The cell 4 is mounted on a carriage 5 capable of moving along the frame under the control of a nut 6 engaged on a lead screw 7 controlled by a wheel 8.

The cell 4 and its carriage 5 are fixed to a closure door 38 for the enclosure 1.

The door has a sealing gasket 9 which is pressed against the face of the enclosure.

Thus, merely by turning the wheel 8 it is possible to move the cell into and out from the chamber while at the same time opening and closing the door 38.

Reference is now made to FIG. 2 for a more detailed description of the cell itself.

The cell comprises an outer envelope made up of three portions: an upper portion 11, a lower portion 12, and an intermediate portion 13.

The envelope is very strong and is designed to withstand pressures which may be as great as 1200 bars. This envelope contains an upper piston 14 and a lower piston 15, and between said pistons it delimits an interior volume comprising an upper chamber 16 located in the upper portion 11 of the envelope, a lower chamber 17 located in the lower portion 12 of the envelope, and a connection channel 18 connecting the upper chamber to the lower chamber, said channel passing through the intermediate portion 13. The chambers 16 and 17 are cylindrical. The intermediate portion includes, in a conventional manner, observation portholes disposed on either side of the channel 18, and as a general rule there are two such portholes, one of which is used for lighting and the other of which is used for observation.

These portholes include a system of marks for measuring the level of the separation surface between the liquid phase and the gas phase of the fluid under investigation which is inserted into the internal volume. A dashed-line circle 19 represents the porthole situated behind the connection channel 18 relative to the plane of the figure.

The channel 18 thus constitutes a restriction level with the portholes enabling the internal volume of the three-portion envelope to be measured. This restriction has the purpose of increasing the sensitivity of variation in the level of the liquid-gas separation surface for a given variation in the volume of the liquid phase, for example, and that of increasing the accuracy of measurement. All three portions of the internal volume, i.e. the upper chamber, the lower chamber, and the connection channel, contain means for inserting and removing fluid. In the example shown in FIG. 2, these means are constituted by channels 20, 21, and 22 fitted with respective stoppers 23, 24 and 25, however the stoppers could easily be replaced by valves under actuator control from outside the enclosure 1 using a control box 39 (see FIG. 1) with appropriate connections being made when the cell 4 is inserted into the enclosure 1. The lower chamber 17 is provided with means 26 in the same manner for connection to a pressure sensor.

The upper piston 14 is connected to the rod 27 of a first hydraulic actuator 28 (see FIG. 1), and the lower piston 15 is connected to the rod 29 of a second hydraulic actuator 30 (see FIG. 1).

These two actuators 28 and 30 are independently powered via ducts 31 and 32. Depending on the nature of the tests to be performed, the actuators may be servo-controlled either as a function of position (in order to perform constant volume measurements) or else as a function of force (in order to perform constant pressure measurements). Naturally, other forms of actuator could be used instead of the hydraulic actuators 28 and 30, for example mechanical actuators could be used.

The lower piston 15 serves to adjust the level of the liquid/gas separation surface, and the upper piston 14 serves to adjust the pressure.

The axes of the upper and lower chambers 16 and 17, and similarly the axes of the actuators 28 and 30, could well be vertically aligned. However, it is preferable for the lower chamber 17 and the second actuator 30 to be disposed horizontally and for the upper chamber 16 and its actuator 28 to be inclined at an angle of about 15° to the horizontal, thereby enabling the equipment to take up less space. The upper chamber is at an angle to the horizontal in order to ensure that there is no risk of a few drops of liquid remaining in the upper chamber 16 which could occur if the upper chamber 16 was horizontal like the lower chamber.

The intermediate portion 13 of the envelope is situated between the upper portion 11 and the lower portion 12 at their ends which are closest together and in such a manner that the connection channel 18 is vertical. The channel 18 opens out into the lowest point of the upper chamber 16.

The free side of each piston is provided with a small propeller for agitating the fluid being investigated: the piston 14 has a propeller 31 and the piston 15 has a propeller 32.

Each piston is provided with a sealing piston ring 33 or 34 which is compressed by a ring 35 or 36 which is screwed onto the piston.

Such a cell may be used for performing measurements to enable curves to be plotted, eg. pressure as a function of temperature for constant volume or volume as a function of temperature at constant pressure.

The portholes and their markings serve to measure the level of the gas/liquid separation and to immediately determine the volume of the liquid.

We claim:

1. In a cell for analyzing a fluid which is condensable, at least in part, said cell forming a volume in which the fluid is inserted, said volume being delimited firstly by an outer envelope and secondly by an upper piston slidably mounted in a sealed manner in said outer envelope and means for slidably shifting said upper piston for adjusting the pressure of the fluid being analyzed, lower means within said outer envelope for adjusting the level of the gas/liquid separation surface, said outer envelope including portholes for displaying and measuring the level of said surface, means provided between the piston and said lower means for inserting the fluid to be analyzed into said volume and for emptying said volume of said fluid, the improvement wherein said means for slidably shifting said upper piston comprises a rod of a first control actuator linked to said upper piston, and said lower means for adjusting the level of said gas/liquid separation surface includes a lower piston slidably mounted within said outer envelope connected to a rod of a second control actuator.

2. A cell according to claim 1, wherein said internal volume includes a restriction at the level of said portholes for observation and measurement, thereby dividing said volume into an upper chamber and a lower chamber which are interconnected by said restriction which constitutes a connecting channel.

3. A cell according to claim 2, wherein said outer envelope comprises three envelope portions, namely an upper portion housing said upper chamber, an intermediate portion including said portholes and having said connection channel passing therethrough, and a lower portion housing said lower chamber, said lower portion and said second actuator being disposed horizontally, said upper portion and said first actuator being slightly inclined relative to the horizontal, said upper and lower portions having ends close together, and the intermediate portion being situated between said upper and lower portions at their ends which are close together, said connection channel being vertical and opening out into the lowest point of said upper chamber.

4. A cell according to claim 3, wherein said slope is about 15°.

5. A cell according to claim 1, further comprising an agitator device on each piston to the side of the piston remote from its actuator rod.

* * * * *